(12) United States Patent
Stamler et al.

(10) Patent No.: US 8,217,006 B2
(45) Date of Patent: *Jul. 10, 2012

(54) INHIBITING GS-FDH TO MODULATE NO BIOACTIVITY

(75) Inventors: Jonathan S. Stamler, Chapel Hill, NC (US); Limin Liu, Durham, NC (US); Alfred Hausladen, Durham, NC (US); Raphael Nudelman, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/566,006

(22) Filed: Sep. 24, 2009

(65) Prior Publication Data

US 2010/0015121 A1 Jan. 21, 2010

Related U.S. Application Data

(60) Continuation of application No. 11/648,406, filed on Dec. 29, 2006, now Pat. No. 7,615,535, which is a division of application No. 09/757,610, filed on Jan. 11, 2001, now Pat. No. 7,179,791.

(51) Int. Cl.
*A61K 38/44* (2006.01)

(52) U.S. Cl. ........... 514/18; 514/1.1; 514/473; 424/94.4

(58) Field of Classification Search .................... None
See application file for complete search history.

(56) References Cited

U.S. PATENT DOCUMENTS

| 3,880,995 | A | 4/1975 | Jones |
| 4,948,793 | A | 8/1990 | Allison et al. |
| 5,444,072 | A | 8/1995 | Patterson et al. |
| 5,648,393 | A | 7/1997 | Stamler et al. |
| 6,057,367 | A | 5/2000 | Stamler et al. |
| 6,150,337 | A | 11/2000 | Tam |
| 6,159,500 | A | 12/2000 | Demopoulos et al. |
| 6,204,248 | B1 | 3/2001 | Demopoulos et al. |
| 7,045,152 | B2 | 5/2006 | Stamler |
| 7,179,791 | B2 * | 2/2007 | Stamler et al. ............... 514/2.4 |
| 7,615,535 | B2 * | 11/2009 | Stamler et al. ............... 514/18 |

FOREIGN PATENT DOCUMENTS

| WO | WO 85/00108 | 1/1985 |
| WO | WO 94/01105 | 1/1994 |
| WO | WO 94/12184 | 6/1994 |
| WO | WO 95/22538 | 8/1995 |
| WO | WO 99/64016 | 12/1999 |
| WO | WO 00/37097 | 6/2000 |
| WO | WO 01/00611 | 1/2001 |

OTHER PUBLICATIONS

Dermer, "Another Anniversary for the Way on Cancer", Bio/Technology (1994), 12:320.
Gura, "Systems for identifying new drugs are often faulty", Science (1997), 278:1041-1042.
Jensen et al., "S-Nitrosoglutathione is a substrate for rat alcohol dehydrogenase class III isoenzyme", Biochem. J. (1998), 331: 659-668.
Jensen et al., "Denitrosation of 1, 3-Dimethyl-2-cyano-1-nitrosoguanidine in Rat Primary Hepatocyte Cultures", Biochemical Pharmacology (1997), 53:1297-1305.
Kuwada et al., "Studies on the Enzymatic Reduction of C-Nitroso Compounds", J. Biochem (1980), 88:859-869.
Liu et al., "A metabolic enzyme for S-nitrosothiol conserved from bacteria to humans", Nature (2001), 410:490-494.

* cited by examiner

*Primary Examiner* — Christopher R. Tate
*Assistant Examiner* — Roy Teller
(74) *Attorney, Agent, or Firm* — Mintz Levin Cohn Ferris Glovsky and Popeo, P.C.; Ivor R. Elrifi; Matthew Pavao

(57) ABSTRACT

Patients needing NO donor therapy or inhibition of pathologically proliferating cells or increased NO bioactivity are treated with a therapeutically effective amount of an inhibitor of glutathione-dependent formaldehyde dehydrogenase.

8 Claims, No Drawings

INHIBITING GS-FDH TO MODULATE NO BIOACTIVITY

RELATED APPLICATIONS

This patent application is a Continuation of U.S. application Ser. No. 11/648,406, filed Dec. 29, 2006, which is a Divisional of U.S. application Ser. No. 09/757,610, filed Jan. 11, 2002, now issued U.S. Pat. No. 7,179,791, each of which are herein incorporated by reference in their entireties.

TECHNICAL FIELD

The invention relates to modulating NO (nitric oxide) bioactivity to obtain therapeutic effects.

BACKGROUND OF THE INVENTION

Stamler et al. U.S. Pat. No. 6,057,367 is directed to treating mammals for infections or for conditions associated with pathologically proliferating mammalian cell growth (for example, certain cancers, restenosis, benign prostatic hypertrophy) by administration of a manipulator of nitrosative stress (an impetus for NO or NO.sub.2 group attachment to proteins, nucleic acids or other biological molecules) to selectively kill or reduce the growth of the microbes or helminths causing the infection or of host cells infected with the microbes or of the pathologically proliferating mammalian cells.

Stamler et al. U.S. application Ser. No. 09/695,934 discloses use of NO donors to prevent the occurrence of restenosis following angioplasty, to inhibit platelets to prevent coagulation and thrombus formation, to treat angina in patients at risk for coagulation and thrombus formation, to inhibit microbes, to treat impotence, asthma, cystic fibrosis, hypoxia and ischemic disorders, heart failure, stroke, arthritis, ARDS, hypertension, neurodegeneration, painful crisis of sickle cell disease, cancer and any pathological proliferation of cells and any NMDA related injury. The invention is directed to C-nitroso compounds and use thereof as NO donors.

Gaston, Stamler and Griffith U.S. application Ser. No. 08/403,775 is directed to use of inhibitors of S-nitrosothiol breakdown to treat asthma.

Numerous enzymes have been shown to break down S-nitrosothiols in vitro. These include (a) thioredoxin system (b) glutathione peroxidase, (c) gamma glutamyl transpeptidase, (d) xanthine oxidase, (e) alcohol dehydrogenase Class III, and (f) other classes of alcohol dehydrogenase.

In respect to alcohol dehydrogenases including alcohol dehydrogenase Class III (also known as glutathione-dependent formaldehyde dehydrogenase), see the following publications which present in vitro data: Kuwada, M., et al. J. Biochem. 88, 859-869 (1980); Jensen, D. E., et al., Biochemical Pharmacology 53, 1297-1306 (1997); Jensen, 1). E., et al., Biochem. J. 331, 659-668 (1998).

Despite the in vitro results referred to above, the current perspective is that thiols, ascorbate and copper ions break down S-nitrosothiols in vivo. However, there has been no work heretofore demonstrating how S-nitrosothiols are broken down in vivo.

It has not heretofore been known that inhibition of glutathione-dependent formaldehyde dehydrogenase mediates NO donor therapy, nitrosative stress and NO bioactivity in vivo.

SUMMARY OF THE INVENTION

It has been concluded in the course of making the invention herein that enzyme, namely glutathione-dependent formaldehyde dehydrogenase known heretofore to oxidize the formaldehyde glutathione adduct, S-hydroxymethylglutathione, previously thought to be the major enzyme substrate, fractions in vivo to metabolize S-nitrosoglutathione and protein S-nitrosothiols to modulate NO bioactivity, by controlling the intracellular levels of low mass NO donor compounds and preventing protein nitrosylation from reaching toxic levels.

Based on this, it follows that inhibition of the enzyme potentiates bioactivity in all diseases in which NO donor therapy is indicated, inhibits the proliferation of pathologically proliferating cells, and increases NO bioactivity in diseases where this is beneficial.

One embodiment herein is directed to a method of treating a patient afflicted with a disorder ameliorated by NO donor therapy, said method comprising administering to said patient a therapeutically effective amount of an inhibitor of glutathione-dependent formaldehyde dehydrogenase.

Another embodiment herein is directed to a method for treating a patient afflicted with pathologically proliferating cells, said method comprising administering to said patient a therapeutically effective amount of an inhibitor of glutathione-dependent formaldehyde dehydrogenase. The term "pathologically proliferating cells" is used herein to include pathologic microbes, pathologic helminths, and pathologically proliferating mammalian cells.

Still another embodiment herein is directed to increasing NO bioactivity for pharmacological effect or in the case of diseases associated with a deficiency of NO. This embodiment is directed to a method of treating a patient in need of increased nitric oxide bioactivity, said method comprising administering to said patient a therapeutically effective amount of an inhibitor of glutathione-dependent formaldehyde dehydrogenase.

DETAILED DESCRIPTION

Glutathione-dependent formaldehyde dehydrogenase (GS-FDH) is a known enzyme which is conserved from microbes including bacteria and fungi to mammals. It is also known as alcohol dehydrogenase Class III. It has been identified in a variety of bacteria, yeasts, plants and animals. The proteins from E. coli, S. cerevisiae and mouse macrophages share over 60% amino acid sequence identity. In methylotrophic microorganisms, GS-FDH is induced by methanol to prevent formaldehyde accumulation. The physiological significance of formaldehyde oxidation by GS-FDH is less clear in other microorganisms and animals. In the course of making the invention herein GS-FDH associated NADH-dependent S-nitrosoglutathione reductase activity has been detected in E. coli, in mouse macrophages, in mouse endothelial cells, in mouse smooth muscle cells, in yeasts, and in human HeLa, epithelial and monocyte cells. As used herein, the term "glutathione-dependent formaldehyde dehydrogenase" means enzyme that oxidizes S-hydroxymethylglutathione and also provides NADH-dependent S-nitrosoglutathione reductase activity (i.e., decomposes S-nitrosoglutathione when NASH is present as a required cofactor) and shares at least 60% amino acid sequence identity with eves having the same function from E. coli, S. cerevisiae and mouse macrophages. The glutathione-dependent formaldehyde dehydrogenase may also be referred to as S-nitrosoglutathione reductase.

We turn now to the inhibitors of glutathione-dependent formaldehyde dehydrogenase for use in the three embodiments herein. These compounds inhibit the S-nitrosoglutathione reductase activity of the glutathione-dependent formaldehyde dehydrogenase.

One class of compounds for use herein as the inhibitors of glutathione-dependent formaldehyde dehydrogenase is constituted of competitors for NAD⁺ binding. These inhibitors work by binding to the NAD⁺ cofactor binding site of the enzyme and thereby block the NADH cofactor from binding to the enzyme.

One compound of this class is nicotinamide riboside (NR) which has the structure:

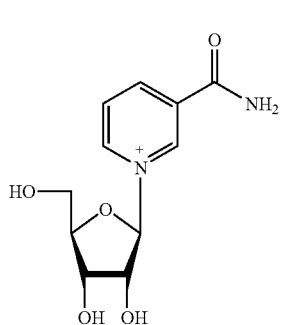

(1)

Other compounds of this class include the following ribonucleoside analogs:

The compound 6-aminonicotinamide (6AN) which has the structure:

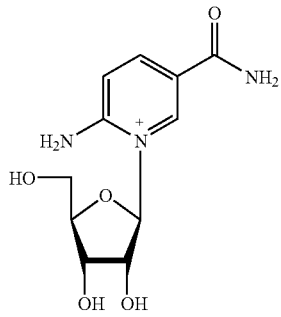

(2)

This compound requires additionally metabolization to 6-amino-NAD(P⁺) by the pentose phosphate pathway (PPP) enzyme, 6-phosphogluconate dehydrogenase, for inhibitory activity.

The compound 5-β-D-ribofuranosylnicotinamide which has the structure:

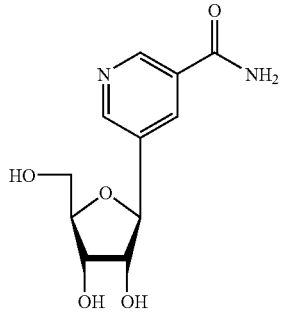

(3)

This compound requires conversion to the corresponding NAD analog, C-NAD, which is described later as Compound (13), for inhibitory activity.

The compound 6-β-D-ribofuranosylpicolinamide which has the structure;

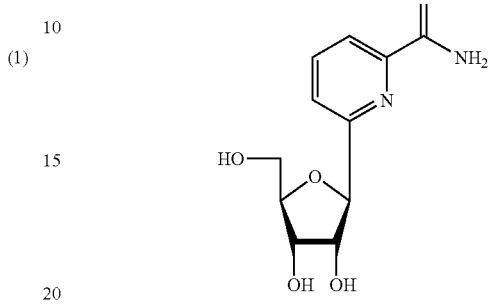

(4)

This compound requires conversion to the corresponding NAD analog, C-NAD, which is described later, as Compound (14), for inhibitory activity.

The compound 2-(3-D-ribofuranosylisonicotinamide which has the structure:

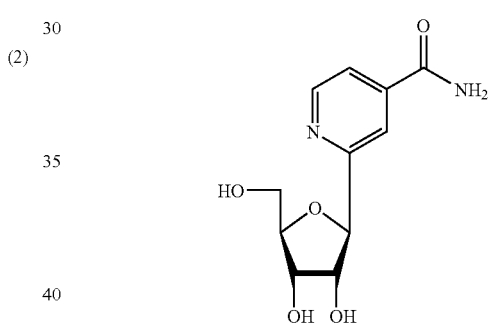

(5)

Other inhibitors of glutathione-dependent formaldehyde dehydrogenase which are ribonucleoside analogs and are competitors for NAD⁺ binding and thereby inhibit the S-nitrosoglutathione reductase activity of GS-FDH have the formula:

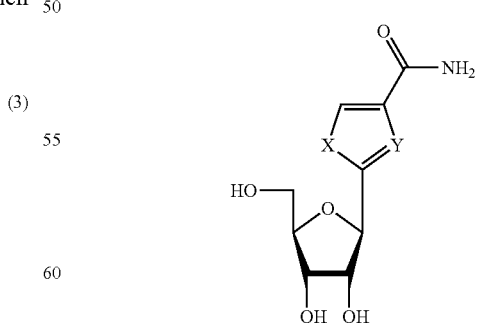

(6)

These include thiophenfurin (5-β-D-ribofuranosylthiophene-3-carboxamide), Compound (6a), which has the formula (6) where X=S and Y=CH; furanfurin (5-β-D-ribofuranosylfuran-3-carboxamide), Compound (6b), which has the formula (6) where X=O and Y=CH; tiazofurin (2-β-D-ribofuranosylthiazole-4-carboxamide), Compound (6c), which has the formula (6) where X=S and Y=N; selenazofurin (2-β-D-ribofuranosylselenazole-4-carboxamide), Compound (6d), which has the formula (6) where X=Se and Y=N; and selenophenfurin (5-β-D-ribofuranosylselenophene-3-carboxamide), Compound (6e), which has the formula (6) where X=Se and Y=CH. These compounds are metabolized to their isosteric NAD analogs for activity. For example, tiazofurin is phosphorylated by adenosine kinase to the 5'-monophosphate and converted by NAD-pyrophosphorylate to TAD, described later, for competitive binding.

Still another ribonucleoside analog which is a competitor for $NAD^+$ binding and thereby inhibits the S-nitrosoglutathione reductase activity of GS-FDH is benzamide ribosome (BR) which has the formla.

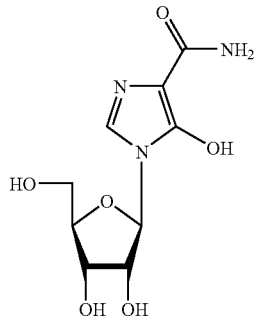

(7)

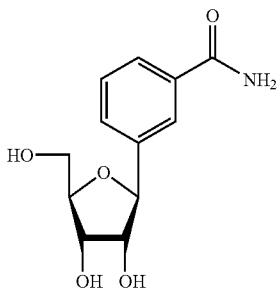

(BR) is metabolized to (BAD), described later, for activity.

Still another ribonucleoside analog which is a competitor for $NAD^+$ binding and thereby inhibits the S-nitrosoglutathione reductase activity of GS-FDH is ribavirin which has the formula:

(8)

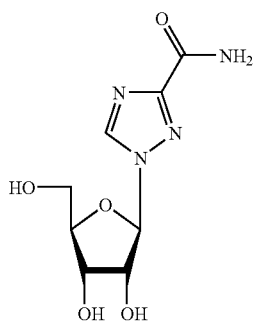

Still another ribonucleoside analog which is a competitor for $NAD^+$ binding and thereby inhibits the S-nitrosoglutathione reductase activity of GS-FDH is mizoribine (MZR) which has the formula.

(9)

Still another ribonucleoside analog for use herein as inhibitor of GS-FDH is 5-ethynyl-1-β-D-ribofuranosylimidazole-4-carboxamide (EICAR) which has the formula:

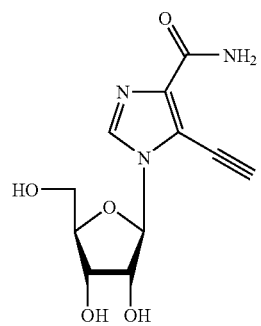

(10)

This compound metabolizes to (EAD), Compound (17) described later, for inhibitory activity.

Another compound which is an inhibitor of GS-FDH by virtue of being a competitor for $NAD^+$ binding is $NAD^+$ which has the formula:

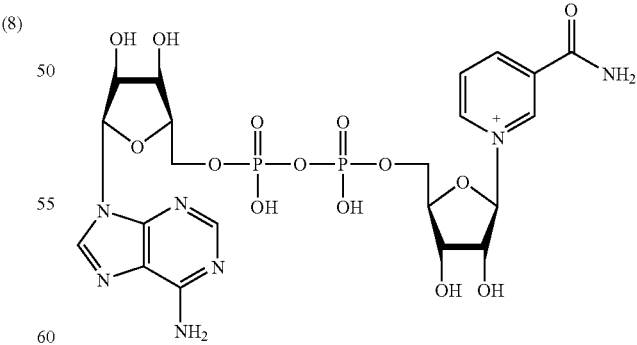

(11)

Still other compounds which are inhibitors of GS-FDH by virtue of being competitors for $NAD^+$ binding and thereby inhibit the S-nitrosoglutathione reductase activity of GS-FDH are $NAD^+$ derivatives.

One such NAD⁺ derivative is 6-amino-NAD which has the formula:

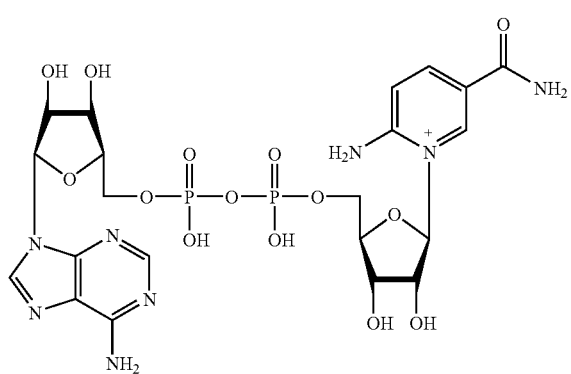

(12)

Another such NAD⁺ derivative is 5-β-D-ribofuranosylnicotinamide adenine dinucleotide (C-NAD) which has the formula:

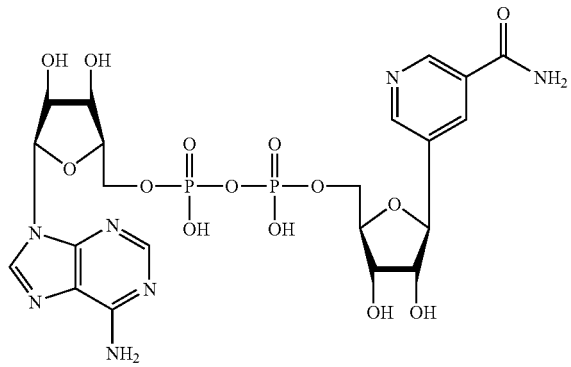

(13)

This compound is a metabolite of Compound (3) described above.

Another such NAD⁺ derivative is 6-β-D-ribofuranosylpicolinamide adenine dinucleotide (C-PAD) which has the formula:

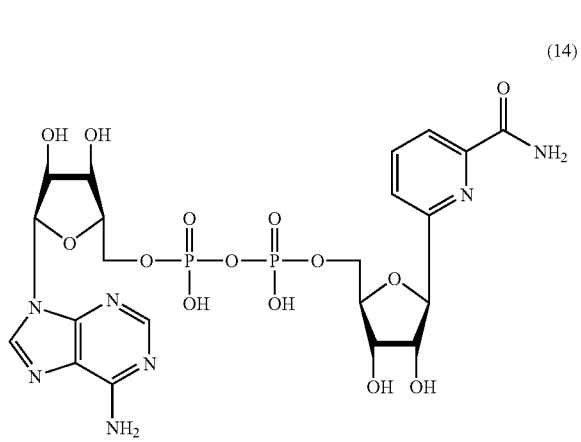

(14)

This compound is a metabolite of Compound (4) described above.

Other such NAD⁺ derivatives have the structural formula:

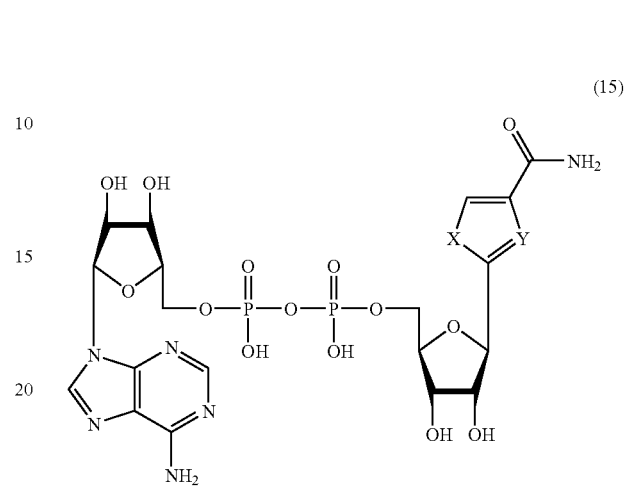

(15)

These include TFAD, Compound (15a), which has the formula (15) where X is S and Y is CH and is a metabolite of Compound (6a); FFAD, Compound (15b), which has the formula (15) where X=O and Y=CH and is a metabolite of Compound (6b); TAD (thiazole-4-carboxamide adenine dinucleotide), Compound (15c), which has the formula (15) where X=S and Y=N and is a metabolite of Compound (6c); SFAD, Compound (15d), which has the formula (15) where X=Se and Y=N, and is a metabolite of Compound (6d); and SAD, Compound (15e), which has the formula (15) where X=Se and Y=CK and is a metabolite of Compound (6e).

Yet another such NAD⁺ derivative is benzamide adenine dinucleotide (BAD) which has the formula:

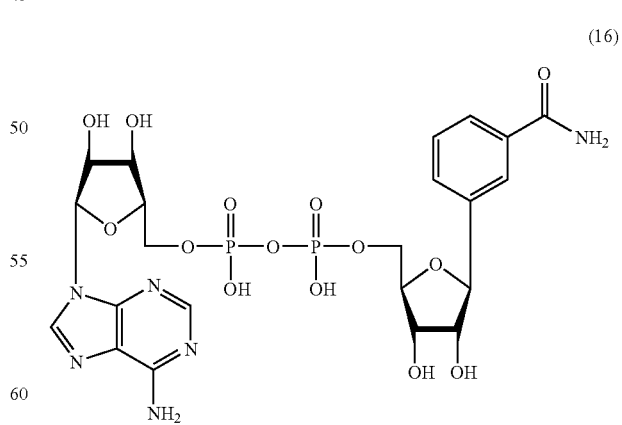

(16)

Compound (16) is a metabolite of (BR) which is Compound (7) described above.

Yet another such NAD+ derivative is (EAD) which has the formula:

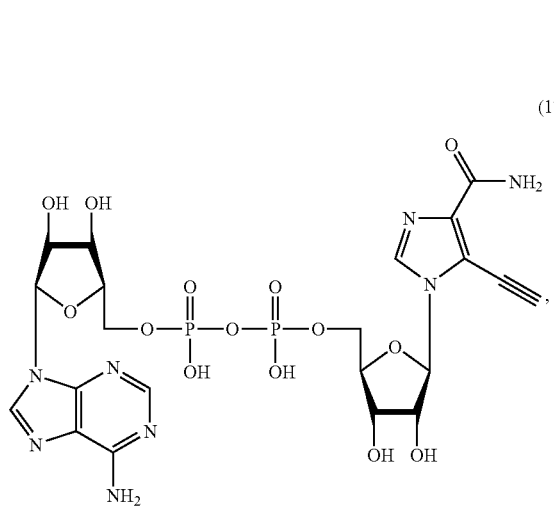

(17)

Compound (17) is a metabolite of EICAR, Compound (10) described above.

Still other such NAD+ derivatives have the formula:

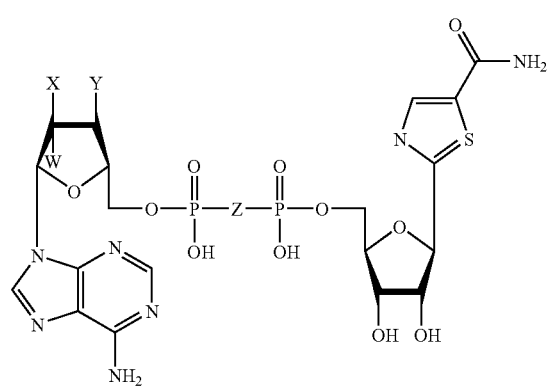

(18)

These include β—CH$_2$-TAD, Compound (18a), which has the formula (18) where X and Y=OH, W=H and Z=CH$_2$; β-CF$_2$-TAD, Compound (18b), which has the formula (18) where X and Y=OH, W=H and Z=CF$_2$; 3'F-TAD, Compound (18c), which has the formula (18) where X=OH, Y=F, W=H and Z=O; 2'Fara-TAD, Compound (18d), which has the formula (18) where X and Y=OH, W=F and Z=O; 2'Fara-β-CH$_2$-TAD, Compound (18e), which has the formula (18) where X and Y=OH, W=F and Z=CH$_2$; and 2'Fara-β-CF$_2$-TAD, Compound (18f), which has the formula (18) where X and Y=OH, W=F and Z=CF$_2$.

Still other such NAD+ derivatives have the formula:

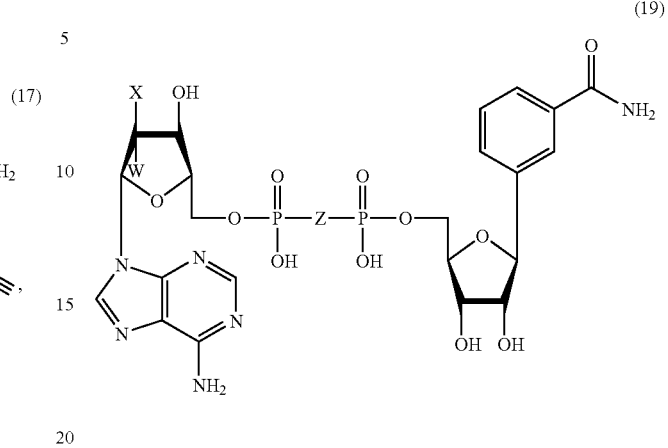

(19)

These include β-CH$_2$—BAD, Compound (19a), which has the formula (19) where X=OH, W=H and Z=CH$_2$, and 2'Fara-β-CH$_2$—BAD, Compound (19b) which has the formula (19) where X=H, W=F and Z=CH.

The derivatives of formulas (18) and (19) including Compounds (18a), (18b), (18c), (18d), (18e), (18f), (19a) and (19b) are TAD (Compound (15c)) and BAD (Compound (16)) analogs which are metabolically stable and cell membrane permeable, methylene or difluoromethylene bis(phosphonate)s, and analogs substituted with fluorine in the ribose moiety of adenosine which are more hydrophobic than their hydroxy congeners.

Other compounds which are inhibitors of GS-FDH are mimickers of the nicotinamide portion of NAD and a water molecule and include mycophenolic acid (MPA), Compound (20), and its morpholinoethyl ester prodrug mycophenolate mofetil (MMF), Compound (21).

Compound (20) has the formula:

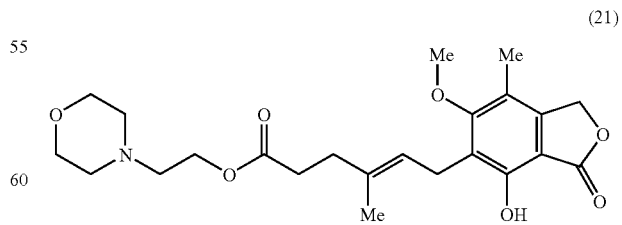

(20)

Compound (21) has the formula:

(21)

Still other compounds which are inhibitors of GS-FDH are competitive substrates for NADH binding. These include 6-thioanologs of natural purine bases, e.g., 6-mercaptopurine (Compound 22) and 6-thioguanine (Compound 23).

Compound (22) has the formula:

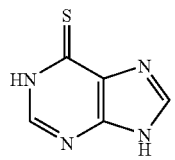
(22)

Compound (23) has the formula:

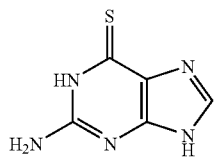
(23)

The above Compounds (1)-(23) are considered also to inhibit the activity of other NADH dependent dehydrogenases such as inosine monophosphate dehydrogenase (IMPDH). Other inhibitors of IMPDH by virtue of competition for $NAD^+$ cofactor binding site, are also effective as inhibitors of GS-FDH herein.

The compounds specifically described above are available commercially or their synthesis is described in or obvious from the literature.

Some of the above compounds have been utilized for some of the utilities herein without knowledge that at least part of their function may have been due to GS-FDH inhibition; these compounds for these uses are excluded from the invention herein, but are not excluded from the invention herein for other uses.

For example, tiazofurin has been used previously for antineoplastic activity against tumors as has thiophenfurin and selenazofurin. Moreover, selenazofurin, ribavirin, MZR, EICAR and MMF have been used for antiviral or potential antiviral activity. Moreover, mycophenolic acid has been evaluated as an anticancer, antiviral, antifungal and antibacterial agent, as well as for its therapeutic use in psoriasis and rheumatoid arthritis. Moreover, furanfurin and ribavirin have been shown to be inactive as an antitumor agents. These cases are excluded from the invention herein. However, the same compounds are not excluded from the invention herein for other uses.

Another class of compounds useful herein to inhibit GS-FDH is constituted of glutathione derivatives including D-glutathione and S-alkyl glutathione containing from 1 to 6 carbon atoms in the S-alkyl group.

The use of gold-based compounds to treat asthma and cystic fibrosis is excluded from the invention herein.

We turn now to the embodiment directed to a method of treating a patient afflicted with a disorder ameliorated by NO donor therapy where the method comprises administering to the patient a therapeutically effective amount of an inhibitor of glutathione-dependent formaldehyde dehydrogenase. This embodiment may be referred to as the first embodiment herein.

The disorders applicable to this embodiment include, for example, breathing disorders (e.g., asthma, cystic fibrosis, and ARDS), heart disease, hypertension, ischemic coronary syndromes, atherosclerosis, glaucoma, diseases characterized by angiogenesis (e.g., coronary artery disease), disorders where there is risk of thrombosis occurring, disorders where there is risk of restenosis occurring, chronic inflammatory diseases (e.g., AID dementia and psoriasis), diseases where there is risk of apoptosis occurring (e.g., heart failure, atherosclerosis, degenerative neurologic disorders, arthritis and liver injury (ischemic or alcoholic)), impotence, obesity caused by eating in response to craving for food, stroke, reperfusion injury (e.g., traumatic muscle injury in heart or lung or crush injury), and disorders where preconditioning of heart or brain for NO protection against subsequent ischemic events is beneficial.

The inhibitors of glutathione-dependent formaldehyde dehydrogenase are described above.

The term "therapeutically effective amount" for this first embodiment means a glutathione-dependent formaldehyde dehydrogenase inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by triponin or CPK.

In general, the dosage, i.e., the therapeutically effective amount, ranges from 1 μg to 10 g/kg and often ranges from 10 μg to 1 g/kg or 10 μg to 100 mg/kg body weight of the patient, per day.

The patients include mammals including humans.

The preferred route of administration is oral administration although other routes of administration including parenteral are useful. Topical administration can be appropriate for localized disorders.

Preferred treating agents for the first embodiment include D-glutathione, ribavirn, D-glutathione together with ribavirin, and mycophenolic acid. D-Glutathione can be given, for example, intravenously at 10-100 mg/kg and/or inhaled in 1-10 M concentration for asthma; inhaled at 1-10 mM concentration for cystic fibrosis and ARDS; and intravenously at 10-300 mg/kg for heart disease including angina, ischemic coronary syndrome, and disease where there is risk of apoptosis occurring (e.g., acetaminophen induced liver injury), and at 100 to 1,000 mg for hypertension. Ribavirin can be given, for example, injected in an amount of 1-10 g at a concentration of 5-25 mg/ml for angina from coronary artery disease, inhaled in amount of 1 to 10 grams to prevent thrombosis from occurring, e.g., where pulmonary embolism is found, and topically at 1-5% in a topical composition for psoriasis. Mycophenolic acid can be given, for example, coated on a stent (drug concentration 10-40% per polymer) for treating restenosis or topically at a concentration of 1 to 10% in a paste to treat impotence.

Treatment is continued as long as symptoms and/or pathology ameliorate.

We turn now to the embodiment directed to a method of treating a patient afflicted with pathologically proliferating cells where the method comprises administering to said patient a therapeutically effective amount of an inhibitor of glutathione-dependent formaldehyde dehydrogenase. This embodiment may be referred to as the second embodiment herein.

We turn now to the case of the second embodiment herein where the pathologically proliferating cells are pathologically proliferating microbes.

The microbes involved are those where glutathione-dependent formaldehyde dehydrogenase is expressed to protect the microbe from nitrosative stress or where host cell infected with said microbe expresses said enzyme thereby protecting the microbe from nitrosative stress.

The term "pathologically proliferating microbes" is used herein to mean pathologic microorganisms including but not limited to pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367 which are incorporated here by reference.

The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium* leper (leprosy), or *Salmonella typhi* (typhoid fever).

We turn now to the case of the second embodiment herein where the pathologically proliferating cells are pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367 which is incorporated herein by reference.

We turn now to the case of the second embodiment where the pathologically proliferating cells are pathologically proliferating mammalian cells.

The term "pathologically proliferating mammalian cells" as used herein means cells of the mammal that grow in size or number in said mammal so as to cause a deleterious effect in the mammal or its organs. The term includes, for example, pathologically proliferating cancer cells, the pathologically proliferating or enlarging cells causing restenosis, the pathologically proliferating or enlarging cells causing benign prostatic hypertrophy, the pathologically proliferating cells causing myocardial hypertrophy and proliferating cells at inflammatory sites such as synovial cells in arthritis. Pathologically proliferating cancer cells include the cell proliferation in Hodgkin's disease, in small cell lung cancer, in cancer of the breast, and in testicular and prostate cancer.

The inhibitors of glutathione-dependent formaldehyde dehydrogenase for this second embodiment herein are those described above.

The therapeutically effective amount for this second embodiment means a glutathione-dependent formaldehyde dehydrogenase inhibiting amount in vivo which is an antiproliferative effective amount. Such antiproliferative effective amount as used herein means an amount causing reduction in rate of proliferation of at lest 10%.

In general, the dosage, i.e., the therapeutically effective or antiproliferative effective amount, ranges from 1 µg to 10 g/kg and often ranges from 10 µg to 1 g/kg or 10 µg to 100 mg/kg body weight of the patient being treated, per day.

The patients are mammals including humans.

The preferred route of administration in respect to inhibiting growth of microbes is oral administration although other routes of administration including parenteral and topical are useful. Topical administration is especially useful for exposed infections, e.g., fungal infections such as athlete's foot, viral infections such as herpes and microbe-caused oral or skin lesions. For inhibiting the growth of helminths, the preferred route of administration is oral administration although other routes of administration including parenteral are useful. For inhibiting the growth of pathologically proliferating cancer cells, the route of administration can be oral or parenteral and local administration is possible, for example, by infusion directly into a tumor or into the blood vessels delivering blood to the tumor, or by forming the agent into a slow release pellet or into a polymer matrix and then implanting the pellet or polymer matrix device in or on the tumor. The preferred routes of administration in the case of inhibiting growth of pathologically proliferating mammalian cells that would cause restenosis is from attachment on a stent implanted in angioplasty but systemic including oral and intravenous administration can be acceptable. The preferred route of administration in the case of inhibiting growth of pathologically proliferating mammalian cells causing benign prostatic hypertrophy is from attachment on a prostatic implant or by local injection.

Where the pathologically proliferating cells comprise pathologic bacteria or fungus and the patient is afflicted with a bacterial or fungal infection, the administering kills or reduces the growth of the pathologic bacteria or fungus. Where the pathologically proliferating cells are pathologically proliferating mammalian cells, the administering kills or reduces the growth of the pathologically proliferating mammalian cells.

Preferred treating agents for the second embodiment include D-glutathione, ribavirin, D-glutathione together with ribavirin, and mycophenolic acid. D-Glutathione can be given, for example, inhaled at 1-10 mM concentration for viral pneumonia; orally at a dose of 0.2 to 2 grams daily for pinworm and Hodgkin's disease, to inhibit restenosis after angioplasty and to resolve benign prostatic hypertrophy; and intravenously at 100 to 300 mg/kg for squamous cell lung cancer. The combination of D-glutathione and ribavirin is preferably given for bacterial pneumonia (e.g., 100 mg-1 g D-glutathione orally and 1-10 g ribavirin inhaled) and for metastatic breast cancer, metastatic testicular cancer and metastatic prostate cancer (e.g., 100-300 grams/kg D-glutathione intravenously up to four times or more a day and 1-10 g ribavirin intravenously).

Treatment is continued as long as symptoms and/or pathology ameliorate.

The inhibitor of glutathione-dependent formaldehyde dehydrogenase can be administered alone for the second embodiment or in combination with conventional therapy for the disorder being treated or in combination with newly discovered agents for use for therapy of the disorder treated and/or in combination with any other agent that imposes nitrosative or oxidative stress.

Agents for selectively imposing nitrosative stress to inhibit proliferation of pathologically proliferating cells in combination therapy with GS-FDH inhibitors herein and dosages and routes of administration therefor include those disclosed in U.S. Pat. No. 6,057,367, the whole of which is incorporated herein.

Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GS-FDH inhibitors herein include, for example, L-buthionine-S-sulfoximine (BSO), glutathione reductase inhibitors (e.g., BCNU), inhibitors or uncouplers of mitochondrial respiration and drugs that increase reactive oxygen species (ROS), e.g., adriamycin, in standard dosages with standard routes of administration. For example, BSO can be given intravenously or orally at 10-30 grams per day.

We turn now to the embodiment directed to a method of treating a patient in need of increased nitric oxide bioactivity, said method comprising administering to said patient a therapeutically effective amount of an inhibitor of glutathione-dependent formaldehyde dehydrogenase. This embodiment may be referred to as the third embodiment herein.

In one subset, i.e., the first subset, of the third embodiment, the patient has a disorder associated with a deficiency in nitric oxide. The term "disorder associated with a deficiency in nitric oxide" is used herein mean disorder where NO deficiency is a feature and the deficiency constitutes less NO than the norm or less than the normal NO bioactive response. Disorders associated with a deficiency in nitric oxide include atherosclerosis, restenosis, and disorders involving deficiency in NO in tissues where NO is necessary to keep the tissues alive, e.g., deficiency in NO in endothelial cells, hepatocytes and certain lung sites, including liver diseases comprising inflammatory liver disorders, including, for example, chronic viral hepatitis B, chronic hepatitis C, alcoholic liver injury, drug (including acetaminophen)-induced liver injury, primary biliary cirrhosis, autoimmune hepatitis, nonalcoholic steatohepatitis and liver transplant rejection. For atherosclerosis, the NO deficiency can be detected in serum or in blood vessel responses. For restenosis, the NO deficiency is inherent in the injurious event which removes the source of NO. For liver disorders, the NO deficiency is detected in liver tissue.

The inhibitors of glutathione-dependent formaldehyde dehydrogenase for the first subset of the third embodiment are those described above.

The term "therapeutically effective amount" for the first subset of the third embodiment means a glutathione-dependent formaldehyde dehydrogenase inhibiting amount in vivo that causes amelioration of the disorder being treated or protects against risk associated with the disorder. For example, for treating atherosclerosis, a therapeutically effective amount is a blood vessel dilating effective amount. For treating restenosis, a therapeutically effective amount is a restenosis inhibiting effective amount. For treating liver diseases and disorders, an effective amount is a liver tissue inflammation ameliorating amount.

In general, the dosage for the first subset of the third embodiment, i.e., the therapeutically effective amount, ranges from 1 µg to 10 g/kg and often ranges from 10 µg to 1 g/kg or 10 µg to 100 mg/kg body weight of the patient, per day.

The patients include mammals including humans.

The preferred routes of administration are oral and parenteral including intravenous with coating on an implanted stent being very appropriate for treating restenosis.

A preferred agent for treating a patient with atherosclerosis is D-glutathione administered by oral route at a dosage ranging from 0.5 to 100 mg/kg.

A preferred agent for treating a patient having or at risk for restenosis is D-glutathione administered on a stent at a dosage ranging from 1 nanomole to 100 micromoles.

A preferred agent for treating liver diseases is D-glutathione administered by intravenous route of administration at a dosage ranging from 1 to 1,000 mg/kg.

Treatment is continued for the first subset of the third embodiment as long as symptoms and/or pathology ameliorate.

In a second subset, i.e., the second subset of the third embodiment, the patient has a disorder where NO bioactivity is beneficially increased for pharmacological effect. For example, in hypertension, NO production may or may not be normal but in either case, pharmacological amounts are required to reverse the blood pressure increase, or in restenosis the blood vessel may heal with restoration of NO production, but more NO may be required to treat process (so no more smooth muscle proliferation). Another disorder that is embraced in the second subset of the third embodiment is heart failure. Still another disorder that is embraced in the second subset of the third embodiment is angina.

The inhibitors of glutathione-dependent formaldehyde dehydrogenase for the second subset of the third embodiment are those described above.

The term "therapeutically effective amount" for the second subset of the third embodiment means a glutathione-dependent formaldehyde dehydrogenase inhibiting amount in vivo that causes amelioration of the disorder being treated or protects against risk associated with the disorder. For example, for treating hypertension, a therapeutically effective amount is a blood pressure lowering effective amount. For preventing occurrence of smooth muscle proliferation after a blood vessel is healed, a therapeutically effective amount is a smooth muscle proliferation inhibiting amount. For treating heart failure, a therapeutically effective amount is an apoptosis inhibiting effective amount. For treating angina, a therapeutically effective amount is an angina ameliorating effective amount.

In general, the dosage for the second subset of the third embodiment, that is, the therapeutically effective amount, ranges from 1 µg to 10 g/kg and often ranges from 10 µg to 1 g/kg or 10 µg to 100 mg/kg body weight of the patient, per day.

The patients include mammals including human.

The preferred routes of administration are oral and parenteral including intravenous with coating on an implanted stent being appropriate to inhibit smooth muscle proliferation after a blood vessel is healed in respect to restenosis.

The preferred agents, dosages and routes of administration in connection with treating hypertension and inhibiting smooth muscle cell proliferation are those described in conjunction with treating hypertension and restenosis vis-a-vis other embodiments herein as described above. Preferred agent for treating heart failure or angina is D-glutathione administered orally at 0.5 to 100 mg/kg.

Treatment is continued for the second subset of the third embodiment for as long as symptoms and/or pathology ameliorate.

The inhibitor of glutathione-dependent formaldehyde dehydrogenase can be administered alone for the third embodiment or in combination with conventional therapy for the disorder being treated or in combination with newly discovered agents for use for therapy of the disorder treated and/or in combination with any other agent that imposes nitrosative stress or which is functional for pharmacological delivery of NO or NO related components for therapeutic application or which upregulates endogenous NO.

The agents for posing nitrosative stress for this case of the third embodiment and dosages and routes of administration therefor are those described for the second embodiment compatible with treatment of the disorders of the third embodiment.

The agents functional for pharmacological delivery of NO or NO related compound have the moiety —$RNO_x$ where R is N, C, S, O or transition metal and x is 1 or 2. These include known agents, e.g., nitroglycerin or nitroprusside used in conventional amounts with conventional routes of administration.

The agents for upregulating endogenous NO include cytokines, e.g., tumor necrosis factor alpha, interferon gamma and interleukin 1β used in conventional amounts with conventional routes of administration, to activate or upregulate NO synthase to make NO, and substrates for NO synthase, e.g., L-arginine (e.g., in an amount of 2-10 grams, e.g., 6 grams per day administered systemically).

For example, patients with angina or hypertension treated with nitrates, i.e., nitroglycerin or nitroprusside standard of care respectively, who are not responding adequately can be given GS-FDH inhibitor, e.g., 1 mM D-glutathione, to increase NO levels.

For example, patients with angina can be treated with nitroglycerin administered in conventional amounts with conventional route of administration concomitantly with inhibitor of glutathione-dependent formaldehyde dehydrogenase, e.g., D-glutathione administered orally at 0.5 to 100 mg/kg or any of the other GSD-FDH inhibitors specifically recited above.

Moreover, for example, patients with malignant hypertension from heart failure treated with nitroprusside in conventional amounts with conventional route of administration can be concomitantly administered GS-FDH inhibitor, e.g., D-glutathione administered orally at 0.5 to 100 mg/kg or any of the other GS-FDH inhibitors specifically recited above.

The mechanism of the invention is shown by the following background example and the invention is illustrated by the following working examples.

Background Example 1

Detection of S-Nitrosoglutathione Reductase Activity in *E. Coli* Lysates

A crude extract (500 μg/ml; *E. coli* strain RK4936) was incubated anaerobically with 0.2 mM NADH in the absence or presence of 0.15 mM S-nitrosoglutathione (GSNO), and NADH consumption (absorbance at 340 in) was followed over time. The experiment was performed anaerobically to eliminate non-specific NADH oxidation by diaphorases present in *E. coli* lysates. In addition, $K_M$ values, $K_{cat}$ values and $K_{cat}/K_M$ values were obtained based on assays using 12 nM enzyme, 0.2 mM NADH and 10-500 μM GSNO using as buffers (100 mM; 0.1 mM DTPA), sodium acetate (OH 4-5), MES (pH 6), BisTrisPropane (pH 7) and Tris (pH 7.5-9). The experiment showed a GSNO-consuming activity in *E. coli* lysates that was dependent on NADH.

Identification of Activity as Glutathione-Dependent Formaldehyde Dehydrogenase (GS-FDH)

The GSNO metabolizing activity from *E. coli* strain RK4936 was purified from 8 liters of stationary phase cells. A 100,000 g supernatant in 20 mM BisTrisPropane (pH 7) was applied to a 5×40 cm Q-Sepharose column and eluted with a linear NaCl gradient in 20 mM BisTrisPropane (pH 7). Active fractions were pooled, adjusted to 1 M $(NH_4)_2SO_4$, and applied to a 2.5×20 cm column of Butyl Sepharose. Elution was done with a decreasing $(NH_4)_2SO_4$ gradient from 1 to 0 M. After gel filtration on a HiPrep 16/10 desalting column (Pharmacia), the enzyme was farther purified on a MonoQ column. Active fractions were applied to a 1.6×10 cm column of AMP Sepharose, washed with 0.15 M NaCl, and eluted with 20 mM $NAD^+$. The protein was pure as judged by SDS-PAGE (yield: 0.52 mg). Limited N-terminal sequencing after blotting onto a PVDF membrane identified the protein as the glutathione-dependent formaldehyde dehydrogenase.

Detection of GS-FDH in Mouse Macrophages

Mouse macrophages RAW264.7 cells (cell line obtained from the ATCC) were stimulated with interferon-gamma and lipopolysaccharide (LPS) for 18 hours as described in Liu, L., et al. Proc. Natl. Acad. Sci. USA 96, 6643 (1999). S-Nitrosothiol levels in the whole lysate, in the fraction of the lysate that passed through a Bio-Gel P-6 column and in the fraction that passed through a 5 kDa out-off ultrafiltration membrane were measured by photolysis-chemiluminescence as described in Mannick, J. G., et al., Science 284, 651 (1999). Amounts of S-nitrosothiol (pmol) were normalized against protein content (mg) of the whole lysate. Data obtained were the mean±SE of three independent experiments. It was found that S-nitrosothiols larger than 5 kDa (high-mass) were present in high amounts in the cells lysate, whereas low mass S-nitrosothiols (<5 kDa) were not detectable (limit of sensitivity 1 pmol S-nitrosoglutathione (GSNO)).

Since GSNO (~300 pm/$10^6$ cells) formed in the extracellular medium of interferon-gamma/LBS-treated RAW 264.7 cells that were incubated with glutathione as described in Akaike, T., et al., J. Biochem (Tokyo) 122, 459 (1997), and glutathione is the predominant source of intracellar thiol (Kosower, N. S., et al., Int. Rev. Cytol. 54, 109 (1978)), we concluded that the reason for the lack of GSNO in our experiment was that it was either rapidly exported or metabolized.

Rates of nitrosothiol accumulation in the medium of RAW 264.7 cells was found to be very slow at the limits of detection, and this result was consistent with what was found in Kosower, N. S., et al., Int. Rev. Cytol. 54, 109 (1978).

To test whether GSNO was being rapidly metabolized, GSNO was incubated in reaction buffer supplemented with NADH or in cell lysates with and without NAD. Cells were homogenized by sonication in a solution containing 20 mM Tris-HCl (pH 8.0), 0.5 mM EDTA, 0.1% NP-40 and 1 mM phenylmethylsulfonyl (PMSF). To detect GSNO-metabolizing activity, 0.86 mg/ml RAW 264.7 lysate was incubated with 100 μM GSNO in reaction buffer (20 mM Tris-HCl (pH 8.0), 0.5 mM EDTA) with 0 or 200 μM NADH at room temperature for various times. Nitrosothiol levels in the reaction mixture were measured by the Saville assay as described in Stamler, J. S., Science 276, 2034 (1997). GSNO-dependent NADH consumption was also measured using either absorbance (OD 340 nm) or fluorescence (340/455 nM) measurements of NADH. The results showed that GSNO was quickly metabolized when it was incubated with extracts from resting macrophages. The same result of GSNO being quickly metabolized was obtained from cytokine activated macrophages. As in E. coli, the GSNO metabolizing activity required NADH and was ineffective at metabolizing alternate nitrosothiols.

GSNO-metabolizing activity of RAW 264.7 cells was recovered in a single function following anion exchange on a MonoQ column. Further purification over a 5' AMP Sepharose column yielded a single band of about 43 kDa in a silver-stained SDS-PAGE gel. To purify the GSNO reductase, the cell lysate was first subjected to stepwise ammonium sulfate precipitation. The GSNO) reductase activity was precipitated between 45-75% ammonium sulfate. After dialysis against 20 mM Tris-HCl (pH 8.0), the proteins were fractionated on a MonoQ column with increasing concentrations of NaCl. The GSNO reductase activity was finally purified with a 5' AMP Sepharose 4B affinity column (Amershem Pharmacia) in 20 mM phosphate buffer. SDS-PAGE and Coomassie blue staining gave the single band of about 43 kDa.

The purified protein was digested by trypsin and the resulting peptides were analyzed by mass spectrometry. Peptide mass database search with GPMAW program identified the protein as mouse GS-FDH(SP-P28474) with high scores, matching 8 fragments (42% coverage) to mouse GS-FDH.

The purified protein also oxidized the formaldehyde-glutathione adduct, S-hydroxymethylglutathione, previously thought to be the major enzyme substrate. The specific activity for this oxidation was only about 6% of the GSNO reducing activity. Thus, GSNO is the preferred substrate of this enzyme.

Kinetic analysis revealed that the purified protein has a $K_M$ of 20 μM and an estimated $K_{cat}$ 5,600 min$^{-1}$ for GSNO. The stoichiometry of GSNO to NADH was found to be one to one.

In summary, the GSNO reductase activity of mouse macrophage cells is remarkably high and specific toward GSNO, and this activity constitutes a major metabolic pathway for GSNO in mouse macrophages. The data indicates that by eliminating endogenous GSNO, GS-FDH protects from nitrosative stress.

Detection in Other Mouse Cells

NADH-dependent GSNO reductase activity was also detected in mouse SVEC4-10 endothelial cells (cell line obtained from the ATCC) and mouse SV40LT-SMC smooth muscle cells (cell lie obtained from the ATCC).

Detection in Human Cells

Testing for NADH-dependent GSNO reductase activity was carried out on human HeLa cells, human epithelial A549 cells, and human monocyte THP-1 cells. The cells were from cell lines obtained from the ATCC. Cells were homogenized by sonication in a solution containing 20 mM Tris-HCl (pH 8.0), 0.5 mM EDTA, 0.1% NP-40 and 1 mM phenylmethylsulfonyl fluoride (PMSF).

GSNO (200 μM) was incubated with 0 or 4 μg/ml of the cell lysates in reaction buffer (20 mM Tris-HCl (pH 8.0), 0.5 mM EDTA) supplemented with NADPH (300 μM), NADPH (300 μM), glutathione (GSH, 2 mM), and ascorbic acid (ASA, 500 μM) in combinations as set forth in the table below, at 37° C. for 5 minutes. After precipitation of the reaction mixtures with trichloroacetic acid (8.3% final concentration), the supernatants were diluted threefold in the buffer and nitrosothiol levels in the reaction mixture were measured by the Saville assay as described in Stamler, J. S., Science 276, 2034 (1997). Data are the mean of two independent experiments.

Data are set forth in the table below where GSNO metabolizing activity is shown as percent of that in the starting material and ASA is ascorbate and GSH is glutathione (ascorbate and glutathione are redox co-factors that have been proposed as decomposing GSNO).

TABLE

|  | No lysate | HeLa | A549 | THP-1 |
|---|---|---|---|---|
| Buffer only | 6.2 | 29.9 | 14.7 | 18.8 |
| +NADH | 0.0 | 84.2 | 72.3 | 90.8 |
| +NADPH + GSH + ASA | 0.7 | 35.4 | 43.9 | 22.6 |

The results indicate GSNO reductase activity was widespread in various human cell lines.

It is Already Known that GS-FDH is Highly Conserved from Bacteria to Mammals

Publications indicating that GS-FDH is highly conserved from bacteria to fungi and mammals are (1) Danielsson, O., et al., Proc. Natl. Acad. Sci. USA 91, 4980 (1994); (2) Shafquat, J., et al., Proc. Natl. Acad. Sci. USA 93, 5595 (1996); (3) Wach, A., et al., Yeast 10, 1793 (1994); (4) Gutheil, W. G., et al., Biochemistry 31, 475 (1999); (5) Wehner, E. P., et al., Mol. Gen. Genet. 237, 351 (1993), and (6) Barber, R. D., et al., J. Bacterial 178, 1386 (1996). The proteins from E. coli, S. cerevisiae and mouse macrophages share over 60% of amino and sequence identity.

Mutant Cells Deficient on GS-FDH Accumulate Increased Levels of GSNO and Protein Nitrosothiols In cases of conservation of genetic function, because of ease of genetic manipulation, yeasts are often used to identify and characterize mammalian genes. See Cardenas, M. E., et al., Clin. Microbiol. Rev. 12, 583 (1999).

As a first step in using this thesis, yeast strain Y190 cells (Clontech; Genbank Accession No. Z74216) were tested for GSNO reductase activity. GSNO was incubated in buffer or lysate of the yeast cells. The test shows the yeast strain Y190 cells have robust GSNO reductase activity.

The entire open reading frame of the GS-FDH/GSNO reductase gene described in Wehner, E. P., et al., Mol. Gen. Genet. 237, 351 (1993) (SFA1/YDL168w) was replaced with dominant selectable cassettes Kan 2 (resistant to G418) or hphMX (resistant to hydromycin) by direct targeting as described in Wach, A., et al., Yeast 10, 1793 (1994). KanMX2 is described in Wach, A. et al., Yeast 10, 1793 (1994). hphMX is described in Goldstein and MeCuskler, Yeast 15, 1541 (1991). Comprehensive analyses of sfa1 (gs-fdh) mutant yeast (4G418$^r$ and 4hygromycin$^r$ clones) showed they lost all GSNO reductase activity.

Replacement of the SFA1 gene with KanMX2 and hph was also carried out in the diploid yeast strain JK93d. After the cassette positively targeted one of the two alleles, diploid cells resistant to either G418 or hydromycin were induced to sporulate. Haploid clones of wild-type and mutant cells obtained by tetrad dissection revealed the loss of GSNO reductase activity co-segregated with resistance to antibiotics (G418$^r$ or hyg$^r$). A 2:2 ratio was seen in all four complete tetrads studied.

When wild-type Y190 yeast cells were treated with GSNO, the yeast accumulated only low levels of nitrosothiols, all of which were high mass (i.e., retained by a 5 kDa cut-off filter).

In contrast, the nitrosothiol levels were more than 11-fold higher in isogenic sfa1 mutants (both sfa1Δ::G418$^r$ and sfa1Δ::hygromycin$^r$) and substantial amounts of low-mass nitrosothiols were detected. This low-mass nitrosothiol pool was completely metabolized by addition of GSNO reductase, thus identifying the low-mass nitrosothiol as GSNO.

Growth of sfa1 mutant cells (both G418$^r$ and hygromicin$^r$ clones) was markedly inhibited by GSNO at concentrations that had little effect on wild-type Y190 cells.

The mutant cells were no more sensitive to the toxic effects of $H_2O_2$ than wild-type Y190 cells.

These data show that GS-FDH/GSNO reductase is essential for protection of nitrosative stress in yeast; whereas it offers no resistance to oxidative stress. The protection is conferred by metabolizing GSNO directly.

NO Synthase Activation and GSNO

Measurement in Mouse Hepatoytes

Hepatocytes of wild-type mice and their GS-FDH$^{-/-}$ littermates were harvested after perfusion of the livers with Liberase (Roche), and purified by repeated differential sedimentation at 50×g, followed by centrifugation over a 30% Percoll solution. Hepatocytes (over 95% viability by trypan blue exclusion) were plated at a density of $2 \times 10^4$ cells/cm$^2$ in gelatin-coated flasks, and incubated for 24 hours. The cells were then cultured in the presence of recombinant mouse tumor necrosis factor-α (500 units/ml), interferon-gamma (100 units/ml), interleukin-1β (200 units/ml) and lipopolysaccharide (LPS, 10 μg/ml; *E. coli* 0128:B12; Sigma) for 14 and 40 hours. Nitrosylation levels in hepatocytes were measured as described in Eu, J., et al., Biochemistry 39, 1040-1047 (2000). Data showed total nitrosothiol but not alternative NO complexes, were approximately 50% higher in cells deficient in GS-FDH and that the majority of nitrosothiol was bound to protein. Moreover, whereas GSNO was barely detectable in wild-type hepatocytes, the levels increased by 60-175% in GS-FDH$^4$ cells. It is known that such increases protect from liver injury. See Liu, L. and Stamler, J. S., Cell Death and Differentiation 6, 937-942 (1999). The data suggest that inhibiting GS-FDH will protect liver cells from ischemic injury.

Detection in Tissues

Liver tissues from wild-type and GS-FDH-deficient mice were homogenized in an enzyme reaction buffer (phosphate-buffered saline, GIBCO 14190-144, supplemented with 0.1% NP-40 and 1 mM PMSF). GSNO (200 μM) was incubated with 0 or 3 μg/μl of the liver homogenate in buffer supplemented with NADH (300 μM), buffer supplemented with NADPH (300 μM), buffer supplemented with glutathione (2 mM), buffer supplemented with ascorbic acid (500 μM) or buffer supplemented with NADPH (300 μM), glutathione (2 mM), and ascorbic acid (500 μM), at 37° C. for 5 minutes. After precipitation of the reaction mixture with trichloroacetic acid (8.3% final concentration), the supernatants were diluted three-fold in the buffer and nitrosothiol levels were measured by the Saville assay as described in Stamler, J. S., Science 276, 2034 (1997). Data are the mean of two independent experiments. These studies showed that the NADH-dependent GSNO reductase activity dominates alternative decomposition reactions that operate in simplified in vitro systems.

GS-FDH Deficiency Protects in the Case of Liver Injury

Cells dislodged by perfusion and purified as described above, from an injured mouse liver (injured by cytokine administration), treated with 1 millimolar N$^G$-methyl-L-arginine nitric oxide synthase inhibitor (20% activity left), were found to die.

Cells that were the same but deficient in GS-FDH died to a lesser extent, indicating that inhibiting GS-FDH protects injured liver cells.

Working examples illustrating the invention, follow.

Example I

A 25-year-old white female presents to the Emergency Room wheezing with an FEV1 of 1 liter. She is given an intravenous infusion of D-glutathione 50 mg/kg Q.6 hours and her breathing improves. She is subsequently given inhaled D-glutathione (nebulized solution of 10 mM D-glutathione in 3 cc of normal saline) to be taken twice daily.

Example II

A 17-year-old male with cystic fibrosis presents to the Emergency Room with difficulty breathing and a fever. He is given an inhaled treatment of S-nitrosoglutathione (10 mM in 3 cc normal saline) in combination with D-glutathione (3 mM in 10 cc normal saline). His symptoms resolve over the following day.

Example III

A 40-year-old female develops ARDS as a complication of urosepsis. She is intubated and transferred to the Intensive Care Unit. Her blood gas shows a PO, of 60 mm Hg on 100% oxygen. She is given an inhaled dose of 10 mM D-glutathione (in 3 cc normal saline) with an increase in $PO_2$ to 80 mm/Hg, seen over 1 hour.

Example IV

A 70-year-old male status post CABG×2 presents with unstable angina. He is treated with betablockers and nitrates but continues to experience chest pain. An intravenous infusion of 100 mg per kg D-glutathione is given Q6 hours with relief of his symptoms. This k an example of treating heart disease.

Example V

A 60-year-old white male presents to his primary care physician. On routine physical exam his blood pressure is 160/90. The patient is begun on 600 milligrams of D-glutathione BID. On follow-up examination three weeks later, his blood pressure is 140/80.

Example VI

The heart disease treated in Example IV is ischemic coronary syndrome, so Example IV is also an example of treating ischemic coronary syndrome.

Example VII

A 60-year-old white male who undergoes cardiac catheterization and an acetylcholine infusion, shows impaired relaxation (earliest marker of atherosclerosis). The patient is treated with D-glutathione, 600 mg TID for a week. Upon retesting, the patient shows an improved response to acetylcholine.

Example VIII

A 65-year-old male with intractable angina is administered ribavirn as 6 grams diluted to a final volume of 300 cc in sterile water and injected at a final concentration of 20 milligrams per milliliter, given daily for seven days. The patient's angina had improved by six weeks. This is an example of treating disease characterized by angiogenesis.

Example IX

A 43-year-old female presents with shortness of breath and hemoptysis. A VQ scan shows a pulmonary embolism and the patient is begun on inhaled ribavirn, 6 grams diluted in 300 cc and administered by a small particle aerosol generator. Treatment is carried out for 12 hours/day for three days. The patient shows improvement in symptoms. This is an example of treating a disorder where there is risk of thrombosis occurring.

Example X

A 72-year-old white male presents with chest pain seven days post-angioplasty and cardiac catheterization reveals restenosis. A Nir stent coated with mycophenolic acid (drug concentration of 30% per polymer) was deployed with successful results. The patient was discharged the following day, and did well.

Example XI

A 17-year-old male with chronic psoriasis presents at the dermatologist. A paste comprised of acetylsalicylic acid, 2%, combined with 5% ribavirin was applied topically for 8 hours a day. This was repeated daily for two weeks at which time the psoriatic lesion had resolved. This is an example of treating a patient with a chronic inflammatory disease.

Example XII

A 15-year-old boy presents to the Emergency Room having ingested a toxic dose of Tylenol. Liver fixation tests are elevated. The doctor infuses D-glutathione at 200 milligrams per kilogram every 6 hours with gradual normalization of liver function over the following week. This is an example of treating a patient for a disease where there is risk of apoptosis occurring.

Example XIII

A 70-year-old diabetic with a history of impotence presents to his urologist. He is treated with Viagra but shows no improvement. His physician adds topical mycophenolic acid (5% paste) with good results.

Example XIV

A 40-year-old alcoholic male presents with swollen abdomen and elevated LSTs. The patient is infused with D-glutathione at 200 milligrams per kilogram every 6 hours for two weeks. The swelling and elevated LSTs are reduced.

Example XV

A 52-year-old female presents with pneumonia to the Emergency Room. A sputum culture grows out pseudomonas resistant to antibiotics and she is given D-glutathione, 600 milligrams TID, and inhaled ribavirin 6 gm daily for ten days with a resolution of pneumonia.

Example XVI

A 9-year-old presents to her pediatrician who diagnosis ringworm She applies topical ointment comprised of 5% ribavirin acid daily for a week and the skin lesion resolve.

Example XVII

A 52-year-old female status post lung transplant is admitted to the hospital with viral pneumonia. She is given inhaled 1)-glutathione, 3 mM/3 cc normal saline four times a day with resolution of symptoms of cough and shortness of breath.

Example XVIII

A tape test done by a pediatrician conforms the suspected diagnosis of pinworm The child is given 1 gram of D-glutathione daily for three days and the signs and symptom resolve.

Example XIX

A routine chest X-ray shows the presence of a right upper lobe lung mass in a 55-year-old smoker. Bronchoscopy shows a mass at the take off to the right upper lobe and a biopsy confirms diagnosis of squamous cell cancer. A further work-up shows the patient to be stage 3B. The patient is treated with a regimen including three weeks of D-glutathione intravenously 200 milligrams per kilogram four times a day for two weeks. On restaging, the patient is 3A and thus a candidate for surgery.

Example XX

A 25-year-old has a biopsy done on an axillary node which establishes the diagnosis of Hodgkins disease. The patient is given 1 gram of D-glutathione three times a day for a month with resolution of adenopathy.

Example XXI

A 55-year-old female with metastatic breast cancer, unresponsive to conventional measures, is begun on combination of intravenous ribavirin 6 grams a day for seven days and intravenous D-glutathione, 200 grams per kilogram QID. Symptoms of bone pain in her back resolve after two days.

Example XXII

A 30-year-old white male presents with a testicular mass and metastasis to lung and brain. The diagnosis is metastatic testicular cancer. The patient unresponsive to conventional measures, is begun on combination of intravenous ribavirin 6 grams a day for seven days and intravenous D-glutathione, 200 grams per kilogram QID. Symptom of headache resolve after two days.

Example XXIII

A 65-year-old male presents with highly elevated PSA and metastasis to bone. The diagnosis is metastatic prostate cancer. The prostate cancer is treated with conventional therapy. However, the metastasis to bone is unresponsive to conventional measures. The patient is begun on combination of intravenous ribavirin 6 grams a day for seven days and intravenous D-glutathione, 200 grams per kilogram QID. Symptoms of bone pain in back resolve after two days.

Example XXIV

A 65-year-old male has a stent placed for 90% lesion of the left anterior descending coronary artery. He is sent home on a regimen including D-glutathione, 600 mg P.O. three times a day for a month and does well.

Example XXV

A 55-year-old male complaining of urinary frequency and hesitancy (diagnosis: benign prostatic hypertrophy) is begun on D-glutathione, 600 mg three times a day. His symptoms gradually resolve over the following three months.

Example XXVI

A 27-year-old female with acute viral myocarditis develops severe heart failure. Her EF is 10%, and she is unresponsive to conventional therapy. She is placed on the transplant list. Infusion of D-glutathione, 1 gram TED for 10 days, stabilized her deteriorating course.

Example XXVII

A 60-year-old male presenting with angina is treated with nitroglycerine (0.6 mg sublingually) and responds only partly as evidenced by persistent chest pain. The patient is concomitantly started on D-glutathione, 600 mg TIE, with total relief of symptoms. The other GS-FDH inhibitors specifically recited above can be substituted for D-glutathione in appropriate amounts with similar results.

Example XXVIII

A 65-year-old male presents with heart failure and malignant hypertension. Blood pressure is reduced from 240 to 200 systolic with nitroprusside (1.0 µg/kg/min IV infusion, for 10 minutes) and is reduced further to 160 by coadministration of GS-FDH inhibitor, e.g., D-glutathione, 600 mg, TID.

VARIATIONS

Many variations on the above will be obvious to those skilled in the art. Thus, the scope of the invention is defined by the claims.

What is claimed is:

1. A method for treating a patient afflicted with a disorder ameliorated by NO donor therapy, said therapy comprising administering to said patient a therapeutically effective amount of an inhibitor of glutathione-dependent formaldehyde dehydrogenase wherein the inhibitor is D-glutathione or mycophenolic acid.

2. The method of claim 1 where the patient is afflicted with a breathing disorder.

3. The method of claim 2 where the breathing disorder is asthma.

4. A method for treating a patient in need of increased nitric oxide bioactivity, said method comprising administrating to said patient a therapeutically effective amount of an inhibitor of glutathione-dependent formaldehyde dehydrogenase.

5. The method of claim 4 where the patient is afflicted with atherosclerosis.

6. The method of claim 4 where the patient is afflicted with restenosis.

7. The method of claim 4 where the patient is afflicted with an inflammatory liver disease.

8. The method of claim 4 where the patient is afflicted with heart failure.

* * * * *

UNITED STATES PATENT AND TRADEMARK OFFICE
CERTIFICATE OF CORRECTION

PATENT NO. : 8,217,006 B2
APPLICATION NO. : 12/566006
DATED : July 10, 2012
INVENTOR(S) : Jonathan S. Stamler et al.

It is certified that error appears in the above-identified patent and that said Letters Patent is hereby corrected as shown below:

At column 26, claim number 1, lines 19-20, that portion read "dehydrogenase wherein the inhibitor is D-glutathione or mycophenolic acid" should read --dehydrogenase--.

Signed and Sealed this
Twenty-eighth Day of August, 2012

David J. Kappos
*Director of the United States Patent and Trademark Office*